United States Patent [19]

Raines et al.

[11] 4,237,324

[45] Dec. 2, 1980

[54] PRODUCTION OF MONOGLYCOLS FROM ALKYLENE CARBONATES

[75] Inventors: Dale A. Raines, Wheatridge, Colo.; Oliver C. Ainsworth, Baton Rouge, La.

[73] Assignee: The Dow Chemical Company, Midland, Mich.

[21] Appl. No.: 5,065

[22] Filed: Jan. 22, 1979

[51] Int. Cl.$^3$ ............................................. C07C 31/20
[52] U.S. Cl. ................................................. 568/858
[58] Field of Search ........................................ 568/858

[56] References Cited

U.S. PATENT DOCUMENTS

| | | | |
|---|---|---|---|
| 3,629,343 | 12/1971 | Levin et al. | 568/867 |
| 3,855,320 | 12/1974 | Leach et al. | 568/916 |
| 4,117,250 | 9/1978 | Foster et al. | 568/858 |

FOREIGN PATENT DOCUMENTS 267618  7/1970  U.S.S.R. .................................. 568/858

OTHER PUBLICATIONS

Peppel, "I & EC", vol. 50 No. 5 (May 1958), pp. 767-770.
Tanabe, "Solid Acids and Bases", (1970), Academic Press, pp. 1-2.

*Primary Examiner*—Joseph E. Evans
*Attorney, Agent, or Firm*—A. C. Ancona

[57] ABSTRACT

Alkylene glycols are produced from alkylene carbonates by hydrolysis in the presence of water at temperatures of from about 80° to about 200° C. Catalysts, such as alumina, are employed at temperatures from 80° to about 150° C. and only slightly greater than the stoichiometric amount of water is employed to allow the most efficient use of the process.

4 Claims, No Drawings

PRODUCTION OF MONOGLYCOLS FROM ALKYLENE CARBONATES

BACKGROUND OF THE INVENTION

Present commercial processes for making glycols involve the hydrolysis of alkylene oxides, using a large excess of water with the application of heat with or without a catalyst. Generally, these processes obtain only about 88 percent yield of the monoglycol with the remainder going to make the higher di-, tri-, and tetra-glycols. One disadvantage of the present commercial process is that there is a large excess of water which must be evaporated off in order to obtain pure glycol. This is highly energy intensive. A British patent suggests that alkylene glycols can be made from alkylene oxides using only a small amount of water in the presence of carbon dioxide under 10 to 180 atmospheres of pressure and at temperatures of 80° to 220° C. and in the presence of a catalyst, for example, an alkali metal halide such as potassium iodide or sodium iodide. It is theorized in this reference, British Pat. No. 1,177,877, that the reaction takes place through formation of the carbonate which then hydrolyzes to the glycol. Greater than 90% yields to the mono-glycol are claimed for this process. The present invention uses ethylene carbonate as a starting material together with slightly greater than stoichiometric quantities of water over an alumina catalyst to achieve 98% yields of the mono-glycol.

SUMMARY OF THE INVENTION

Ethylene carbonate, together with slightly greater than a stoichiometric amount of water, is passed over a bed of alumina catalyst at temperatures from about 80° to 200° C. to obtain about 98% mono-ethyleneglycol. Preferred temperatures are in the range of about 120° to 140° C.

DETAILED DESCRIPTION OF THE INVENTION

The lower alkylene glycols may be produced starting with the alkylene carbonates and hydrolyzing these in the presence of catalyst with only slightly greater than stoichiometric amounts of water to obtain the monoglycols in very high yields approaching 100%. Temperatures of from about 80° to about 200° C. are operable, 120° to 140° C. being preferred. At temperatures above about 150° C., the reaction may be conducted in the absence of a catalyst, but the catalyst allows temperatures in the neighborhood of about 90° to about 110° C. to be used. Temperatures below 80° C. require excessively long residence times because of a slower reaction rate. Too high a temperature on the other hand, that is above 200° C., will cause the formation of more of the higher diethylene and triethylene glycols. The ratio of water to the alkylene carbonate is preferably at least about stoichiometric. Any less than that will slow the rate of reaction and favor the formation of the higher glycols. More than about 1.6 moles of water per mole of alkylene carbonate will work to the detriment of the process in that more energy is required to remove the excess water. Residence times of about 30 to about 120 minutes are operable, 60 to 90 minutes being preferred. Pressure is atmospheric or autogenous.

The following examples show the process performed in a batch reaction:

EXAMPLE 1 (ATMOSPHERIC)

Into a flask, fitted with a reflux condenser, was placed 100 grams of activated alumina pellets. To this was added 108 grams of ethylene carbonate and 36 grams of water (a mole ratio of 1.6 moles water per mole of ethylene carbonate). The flask was then heated to 93° C. at atmospheric pressure. Over a period of 52 minutes the temperature was slowly raised to 105° C. The yield of monoethylene glycol was 99% of theoretical.

EXAMPLE 2 (ADDED PRESSURE)

In a pressure vessel the same mole ratio of water to ethylene carbonate was introduced and temperature was raised to 191° to 193° C. The pressure was maintained at 200 psig.; the pressure was released after 106 minutes and, with a conversion of 98.7% of the ethylene carbonate, a yield of 96% monoethylene glycol and 4% diethylene glycol was obtained. No catalyst was used in this preparation.

The following example shows the use of a continuous process employing the catalyst of Example 1:

EXAMPLE 3 (CONTINUOUS)

Through a packed tube of alumina pellets, a mixture of 1.1 to 1 mole ratio of water and ethylene carbonate was passed at 130° C. at atmospheric pressure, with a flow rate of 45 ml. per hour. The effluent upon analysis showed 70% conversion of the ethylene carbonate with a 99% yield of the monoethylene glycol. In the same manner, but employing a 1.6 to 1 mole ratio of water to ethylene carbonate, the mixture was passed over alumina pellets at 130° C. at a flow rate of 13 ml. per hour, the effluent showed a 97% conversion of ethylene carbonate with a 98% yield to monoethylene glycol.

The following example shows the use of a noncatalytic process:

EXAMPLE 4

A (comparative)

In the manner of Example 1, 22 grams of ethylene carbonate and 4.5 grams of water (1/1 mole ratio of water to ethylene carbonate) were heated in the absence of catalyst for one hour at 98° C. No ethylene glycol was formed.

B (comparative)

Substantially the same mole ratio of components was then heated for two hours at a temperature of 106° to 108° C. Analysis of the contents after cooling indicated that 3.3% monoethylene glycol was formed.

C (invention)

In a third experiment employing pressure and much higher temperature, a mixture of 1.6 moles of water per mole of ethylene carbonate was heated to 191°–193° C. under 200 psig for one hour and 50 minutes. Analysis of the contents showed a 98% conversion of ethylene carbonate and a 96% yield of monoethylene glycol, 4% diethylene glycol.

Since the advantages of the present invention are primarily in the saving of energy because less water needs to be evaporated from the product, it is obvious that using the lower temperatures together with a catalyst is to be preferred over the pressure and high temperatures without the catalyst. Nevertheless, either process will work to obtain good yields of the monoglycol by the hydrolysis of ethylene carbonate.

We claim:

1. A process for the production of a monoglycol by hydrolyzing an alkylene carbonate which comprises reacting at least about stoichiometric amounts of water and an alkylene carbonate at a temperature of from about 80° C. to about 200° C., in the presence of alumina as catalyst.

2. The process of claim 1 wherein the reaction time is at least about 30 minutes.

3. The process of claim 1 wherein at least about 10 psig pressure is employed.

4. The process of claim 1 wherein the process is continuous.